United States Patent [19]

Bonse et al.

[11] Patent Number: 4,594,427
[45] Date of Patent: Jun. 10, 1986

[54] PREPARATION OF NOVEL 5-ACYLOXY-4-(5H)-OXAZOLONIUM SALTS SUITED FOR USE AS INTERMEDIATES FOR TRIAZINONE HERBICIDES

[75] Inventors: Gerhard Bonse; Gerhard Marzolph, both of Cologne; Heinz U. Blank, Odenthal, all of Fed. Rep. of Germany

[73] Assignee: Bayer Aktiengesellschaft, Leverkusen, Fed. Rep. of Germany

[21] Appl. No.: 360,495

[22] Filed: Mar. 22, 1982

[30] Foreign Application Priority Data

Apr. 22, 1981 [DE] Fed. Rep. of Germany ....... 3115970

[51] Int. Cl.[4] .................. C07D 413/04; C07D 263/08; C07D 285/08
[52] U.S. Cl. ................................. 548/226; 544/134; 546/209; 548/136
[58] Field of Search ................ 548/226, 136; 544/134; 546/209

[56] References Cited

U.S. PATENT DOCUMENTS

| 4,175,188 | 11/1979 | Klenk et al. | 544/182 |
|---|---|---|---|
| 4,224,226 | 9/1980 | Kleemann et al. | 544/182 |
| 4,315,094 | 2/1982 | Bonse et al. | 544/182 |
| 4,370,498 | 1/1983 | Bonse et al. | 564/155 |

FOREIGN PATENT DOCUMENTS

| 1542873 | 7/1970 | Fed. Rep. of Germany | 544/182 |
|---|---|---|---|
| 1795784 | 6/1975 | Fed. Rep. of Germany | 544/182 |

OTHER PUBLICATIONS

Tetrahedron Letters, vol. 28, Pergamon Press 1972, pp. 4065–4074.
Die Makromolekulare Chemie, vol. 131, 2/17/70, pp. 247–257.
Chemical Abstracts, vol. 93, 1980, p. 740.
Khim. Geterosikl. Soedin, 1977, p. 702.
Zhurnal Organicheskoi Khimii, vol. 12, No. 5, May 1976, p. 1134.
Ukr. chim., vol. 30, No. 3, pp. 265–267, 1964.
Ukr. chim., vol. 30, No. 6, pp. 618, 619, 1964.
Ukr. chim., vol. 32, No. 2, pp. 202–203, 1966.
Thesing et al., "Die Chemie der Acylcyanide", Angewandte Chemie, vol. 68, pp. 425–435 (1956).
Dorofeenko et al., "Synthesis of 4(5-H)-Oxazolonium Salts", Khim. Geterosikl. Soedin, (1977) 5, 702.

Primary Examiner—George F. Lesmes
Assistant Examiner—S. A. Gibson
Attorney, Agent, or Firm—Sprung Horn Kramer & Woods

[57] ABSTRACT

Novel 5-acyloxy-4(5H)-oxazolonium salts of the formula

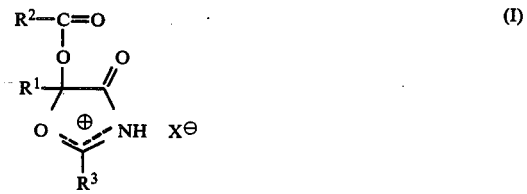

(I)

in which $R^1$ represents an optionally substituted aliphatic group with up to 12 carbon atoms, an optionally substituted cycloalkyl group with 3 to 10 carbon atoms, an optionally substituted phenyl or naphthyl group or an optionally substituted heterocyclic group and $R^2$ and $R^3$ are identical or different and represent a hydrogen atom or an optionally substituted aliphatic group with up to 8 carbon atoms or an optionally substituted phenyl group and $X^\ominus$ represents the anion of an inorganic or organic acid having a $pK_a$ value of less than 2, are obtained in solution when an acyl cyanide of the general formula

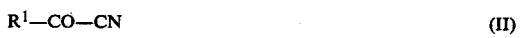

$R^1$—CO—CN    (II)

is reacted with a carboxylic acid anhydride of the general formula

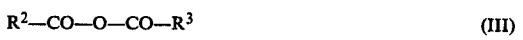

$R^2$—CO—O—CO—$R^3$    (III)

wherein $R^1$, $R^2$ and $R^3$ each have the abovementioned meaning, in the presence of one or more inorganic or organic acids having a $pK_a$ value of less than 2, and if appropriate in the presence of a solvent, and if appropriate at a temperature between 0° and 120° C.

The novel oxazolonium salts (I) can be used as intermediate products for the preparation of known, herbicidally active 3,4,6-trisubstituted 1,2,4-triazin-5(4H)-ones.

4 Claims, No Drawings

PREPARATION OF NOVEL 5-ACYLOXY-4-(5H)-OXAZOLONIUM SALTS SUITED FOR USE AS INTERMEDIATES FOR TRIAZINONE HERBICIDES

The invention relates to certain new 4(5H)-oxazolonium salts having an acyloxy radical in the 5-position, to an unobvious process for their production and to their use as intermediates for the synthesis of known, herbicidally active 3,4,6-trisubstituted 1,2,4-triazin-5(4H)-ones.

4(5H)-Oxazolonium salts which carry hydrogen or lower alkyl groups in the 5-position of the following formula are already known:

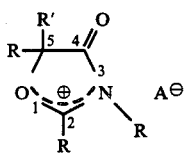

wherein
R = lower alkyl;
R' = hydrogen or lower alkyl;
A = ClO$_4$, Cl or Br

These substances were prepared by reacting α-hydroxycarboxylic acid amides with anhydrides in the presence of 70% strength perchloric acid (Khim. Geterosikl. Soedin 1977, 702; Zh. Org. Khim. 12 (1976) 1134 and U.S.S.R. Pat. No. 159,825 (25.1.1979)) or by reacting α-halogenoacetic acid bromides with amides (Ukr. chim. Z. 30 (1964) 3, 265), or by reacting chloroacetamides with acid chlorides (Ukr. Chim. Z. 30 (1964) 6, 618 and ibid. 32 (1966) 2, 202).

Only 4(5H)-oxazolonium salts which carry hydrogen or alkyl groups in the 5-position can be obtained according to any of the processes described above. 5-Acyloxy-4(5H)-oxazolonium salts are not producible by these methods.

The present invention now provides, as new compounds, the 5-acyloxy-4(5H)-oxazolonium salts of the general formula

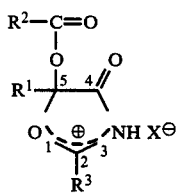

(I)

in which
R$^1$ represents an optionally substituted aliphatic groups with up to 12 carbon atoms, an optionally substituted cycloalkyl group with 3 to 10 carbon atoms, an optionally substituted phenyl or naphthyl group, or an optionally substituted heterocyclic group and
R$^2$ and R$^3$ are identical or different and represent a hydrogen atom or an optionally substituted aliphatic group with up to 8 carbon atoms or an optionally substituted phenyl group and
X$^\ominus$ represents the anion of an inorganic or organic acid having a pK$_a$ value of less than 2

According to the present invention we further provide a process for the production of a compound of the present invention characterized in that an acyl cyanide of the general formula

in which
R$^1$ has the abovementioned meaning,
is reacted with a carboxylic acid anhydride of the general formula

in which
R$^2$ and R$^3$ are identical or different and have the abovementioned meaning,
in the presence of one or more inorganic or organic acids having a pK$_a$ value of less than 2, and, if appropriate, in the presence of a solvent and, if appropriate, at a temperature between 0° and 120° C.

If pivaloyl cyanide and acetic anhydride are used as starting materials and the reaction is carried out in the presence of concentrated sulphuric acid, the course of the reaction according to the present invention is illustrated by the following equation:

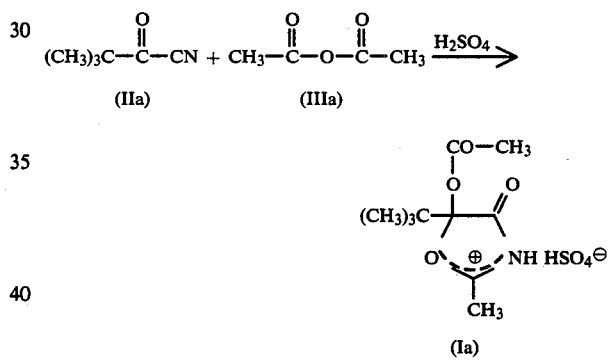

Preferred acyl cyanides of formula (II) to be employed as starting materials are those in which, R$^1$ represents a straight-chain or branched alkyl group with 1 to 4 carbon atoms optionally substituted by alkoxy with 1 to 4 carbon atoms, carbalkoxy with 1 to 4 carbon atoms in the alkoxy part, nitro, nitrile and/or halogen (such as fluorine, chlorine, bromine or iodine); represents a cycloalkyl group with 3 to 6 carbon atoms in the ring system which is optionally substituted by alkyl, alkoxy or carbalkoxy, each with up to 4 carbon atoms, nitro, nitrile and/or halogen (such as fluorine, chlorine and bromine), represents a phenyl or naphthyl group which is optionally substituted by alkyl, alkoxy or carbalkoxy, each with up to 4 carbon atoms, nitro and/or halogen (such as, for example, fluorine, chlorine and bromine); or represents a 5-membered or 6-membered heterocyclic group which contains 1 to 3 hetero-atoms (such as oxygen, sulphur and/or nitrogen) in the ring, is furthermore optionally fused to a benzene ring, and is optionally substituted by alkyl, alkoxy or carbalkoxy, each with up to 4 carbon atoms, nitro, nitrile and/or halogen (such as fluorine, chlorine and bromine).

As examples of heterocyclic radicals which are suitable as radicals R$^1$ there may in particular be mentioned morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

Acyl cyanides of the formula (II) are known and can be prepared according to known processes (compare Angew. Chem. 68, pages 425–435 (1965); also DE-OS (German Published Specifications) Nos. 2,614,240, 2,614,241, 2,614,242, 2,708,182 and 2,708,183).

Pivaloyl cyanide and benzoyl cyanide may be mentioned as acyl cyanides of formula (II) which are particularly preferred for use in the process of the present invention.

Preferred carboxylic acid anhydrides of formula (III) also to be employed as starting materials are those in which $R^2$ and $R^3$ independently represent an optionally chlorine-substituted alkyl group with 1 to 4 carbon atoms, or a phenyl group.

The carboxylic acid anhydrides of the formula (III) are, in some cases, available on an industrial scale and/or preparable in accordance with generally known methods, for example from the corresponding carboxylic acids. Where appropriate, the formation of the carboxylic acid anhydrides of the formula (III) can also be carried out in the reaction medium, using anhydride-forming reagents (such as concentrated sulphuric acid).

Particularly preferred carboxylic acid anhydrides of formula (III), for use in the process of the present invention, are acetic anhydride, propionic anhydride and the anhydrides of the chloroacetic acids.

The reaction according to the invention is carried out in the presence of an acid having a $pK_a$ value of less than 2. Suitable acids of this type are inorganic acids, such as concentrated sulphuric acid, hydrogen halides acids (for example anhydrous hydrogen chloride and hydrogen bromide), as well as perchloric acid and phosphoric acid. Further suitable acids are aliphatic and aromatic sulphonic acids and phosphonic acids as well as halogenoalkanecarboxylic acids (such as trifluoroacetic acid). Preferably, concentrated sulphuric acid is used.

It is possible to carry out the reaction according to the invention in the presence of one or more such acids.

A particular preferred combination of reactants is pivaloyl cyanide as the acyl cyanide of formula (II), acetic anhydride as the carboxylic acid anhydride of formula (III) and concentrated sulphuric acid as the acid.

The reaction temperatures can be varied within a substantial range. In general, the reaction is carried out, as stated above, at temperatures between 0° and 120° C., preferably between about 10° and 60° C.

The reaction is in general carried out under normal pressure.

The reaction can be carried out in the absence or in the presence of a solvent or solubilizing agent. Suitable solubilizing agents are certain organic solvents; glacial acetic acid and methylene chloride are particularly suitable, as are dialkyl ethers (such as diethyl ether or di-isopropyl ether).

In carrying out the process according to the invention, 0.5 to 10 mol, preferably 0.8 to 4 mol, of carboxylic acid anhydride of the formula (III) are in general employed per mol of acyl cyanide of the formula (II); a molar ratio of acyl cyanide of formula (II) to carboxylic acid anhydride of formula (III) of 1:1 to 1:2 is particularly preferred.

The acids required for carrying out the process according to the invention are employed in amounts which range from catalytic quantities to more than stoichiometric quantities. In general, 0.5 to 10 mol, preferably 0.8 to 8 mol, particularly preferentially 1 to 4 mol, of acid are employed per mol of acyl cyanide of formula (II).

A molar ratio of carboxylic acid anhydride of formula (III) to acid of 1:2 is particularly advantageous.

It follows that a molar ratio of acyl cyanide of formula (II) to carboxylic acid anhydride of formula (III) to acid of 1:1:2 to 1:2:4 is very particularly advantageous.

Advantageously, in carrying out the process, the procedure followed is to take the acid and the anhydride, or the mixture of carboxylic acid and anhydride-forming reagent, optionally with addition of a solvent, and to add the acyl cyanide, optionally in a solvent.

The reaction times are in general 1 to 10 hours.

The reaction mixture prepared in accordance with the process described above is a solution of the 5-acyloxy-4(5H)-oxazolonium salts of formula (I) according to the present invention.

The structure of the oxazolonium salts is shown clearly by the IR, $^1$H-NMR and $^{13}$C-NMR spectra of the reaction mixture. This may be illustrated using 5-acetoxy-5-tert.-butyl-2-methyl-4(5H)-oxazolonium ion of the salt of formula (Ia) as an example. The ion is obtained by mixing pivaloyl cyanide, acetic anhydride and anhydrous sulphuric acid in the molar ratio of 1:1:3, in accordance with the procedure described above.

The IR spectrum of this solution shows three strong signals in addition to the bands of the sulphuric acid.

These signals are allocated as follows (see Table 1), in accordance with the comparable data of the known 4(5H)-oxazolonium perchlorates:

The signal at 1830 cm$^{-1}$ is due to the valency vibration of the carbonyl group in the oxazolonium system. It is shifted to higher frequencies as a result of the vicinity of the positive fragment. The signal at 1785 cm$^{-1}$ falls into the absorption range of ester carbonyl groups which are adjacent to electro-negative groups, as, for example, in enol esters. It can, in the present case, be allocated to the 5-acetoxy group. The signals between 1590 and 1530 cm$^{-1}$ can, in conformity with the comparison substances, be allocated to the skeletal vibrations of the oxazolonium nucleus.

TABLE 1

IR spectra of the oxazolonium salts ($\nu$ in cm$^{-1}$)

| Structure | C=O next to O-⊕-NH | O=C-CH$_3$ next to positivated C | O=C-CH$_3$ normal | O-⊕-N skeletal vibration | Literature |
|---|---|---|---|---|---|
|  | 1830 | 1783 | — | 1590, 1570 (Sh), 1530 (Sh) | — |
| 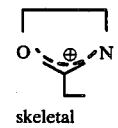 | 1810 | — | 1720 | 1580, 1500 | Zh. Org. Khim. 12(1976) p. 1134 |
| 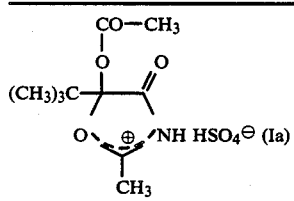 | 1830 | — | — | 1590, 1548–1515 | Khim. Geterosikl. Soedin 1977, 702 |

The $^1$H-NMR spectrum of the solution containing the salt of formula (Ia) shows three signals (Table 2), which are in conformity with the structure of the 4-(5H)-oxazolonium system.

TABLE 2

$^1$H—NMR spectrum of the 4(5H)—oxazolonium salts ($\delta$ in ppm) against tetramethylsilane (TMS) as internal standard

| Structure | Signals | (Allocation) | Solvent |
|---|---|---|---|
|  (Ia) HSO$_4$⊖ | 1.30 (3CH$_3$) | 2.85(CH$_3$—C=O) 3.17(2-CH$_3$) | H$_2$SO$_4$ |
| 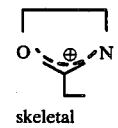 ClO$_4$⊖ | 1.40 (2CH$_3$) | 2.30(CH$_3$CO) 3.08(2-CH$_3$) 4.20(CH$_2$) 5.52(5-CH) | CF$_3$COOH |

(from Zh. Org. Khim. 12, (1976)1134)

The signal at 1.30 ppm, with an integral corresponding to 9 protons, can undoubtedly be allocated to the three methyl groups of the tert.-butyl group. The signal at 3.17 ppm corresponds to a methyl group next to a strongly positivated carbon atom. By comparison with the data in the literature, this signal can be allocated to the 2-methyl group. The signal at 2.85 ppm must be allocated to the 5-acetoxy group. Compared to the acetoxy group of the comparison substance, it is shifted by 0.55 ppm to a lower field. This is due to two effects:

The acetoxy group in the salt of formula (Ia) is bonded to a strongly positivated carbon atom, as a result of which the signal of the CH$_3$ group is shifted towards a lower field. Secondly, sulphuric acid, compared to trifluoroacetic acid as the solvent, causes an additional shift to a lower field, through partial protonation of the ester carbonyl group.

An independent structural proof of the 5-acyloxy-4(5H)-oxazolonium ions present in the reaction mixture is provided by the $^{13}$C-NMR spectra. Measurements were carried out on a reaction mixture of pivaloyl cyanide, acetic anhydride and sulphuric acid in a stoichiometric ratio of 1:2:4.

In addition to the two signals at 189 ppm and 19.5 ppm, which can be allocated to the protonated form of acetic acid, 8 further signals are found (see Table 3), which can be allocated to the eight different carbon atoms of the 5-acetoxy-5-tert.-butyl-4(5H)-oxazolonium ion of the salt of formula (Ia).

The signal at 193 ppm is due to a strongly positivated carbon atom, similar to the acetyl cation. This atom is the 2-C atom of the oxazolonium system. The signals at 171 ppm and 167 ppm can readily be allocated to the carbonyl carbon atoms of the 5-acetoxy group and to the 4-C atom of the oxazolonium system. The signal at 109 ppm corresponds, in the shift position, to a carbon atom between two oxygen atoms, as in ketals, and is, in the present case, allocated to the 5-C atom of the oxazolonium system. The signal at 39.1 ppm corresponds to the tertiary carbon atom and the signal at 22.7 ppm to the primary carbon atoms of the tert.-butyl group. The signals at 20.6 ppm and 17.0 ppm are due to the carbon atoms of the methyl groups on C-2 of the oxazolonium system and in the acetyl group.

in which
R¹ and R³ have the abovementioned meanings,

TABLE 3

| | | ¹³C—NMR spectra (δ in ppm) | | | | | | | |
|---|---|---|---|---|---|---|---|---|---|
| | | Allocation | | | | | | | |
| Substance | Solvent | CH₃—C⊕(O)(O) | CH₃—C⊕(O)(N) | O-C(=O)-C- | -C(=O)-O | -C(=O)-N | -C≡N | -C(O,O)- tertiary C | H₃C—C(O,O) H₃C—C⊕ | H₃C—C⊕(=O) |
| CH₃—C(=O)—O—C(=O)—CH₃ | D₂SO₄ | 189 | | | | | | | | 19.5 |
| CH₃—C⊕(OH)(OH) | | | | | | | | | | |
| (CH₃)₃C—C(=O)—CN | CDCl₃ | | | | 182 | | 112 | 45 | 24.5 | |
| 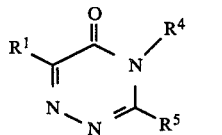 (Ia) | D₂SO₄ | | 193 | 171 | | 167 | | 109 | 39.1  22.7 | 20.6 17.0 |

The 5-acyloxy-4(5H)-oxazolonium salts of formula (I) which can be prepared by the process according to the invention are novel and can be used as intermediates for the preparation of known herbicidally active triazinones (compare, for example, German Pat. Nos. 1,542,873 and 1,795,784).

According to the present invention we thus further provide a process for the production of a 1,2,4-triazin-5(4H)-one of the general formula

in which
R¹ has the abovementioned meaning,
R⁴ represents a hydrogen atom, an alkyl group with 1 to 4 carbon atoms, an aryl group with 6 to 10 carbon atoms or an amino or mono or di-substituted amino group and
R⁵ represents a hydrogen atom, an alkyl group with 1 to 4 carbon atoms, an aryl group with 6 to 10 carbon atoms, a hydroxyl group, an alkoxy group with 1 to 4 carbon atoms, an aryloxy group with 6 to 10 carbon atoms, a mercapto group, an alkylmercapto group with 1 to 4 carbon atoms or an amino or mono- or di-substituted amino group,
characterized in that a 5-acyloxy-4(5H)-oxazolonium salt of formula (I), in solution, is reacted, either directly or after prior hydrolysis to the α-ketocarboxylic acid N-acylamide of the general formula $$R^1-CO-CO-NH-CO-R^3 \quad (V)$$

with a hydrazine derivative of the general formula $$\underset{NH_2-N=C-NH-R^4}{\overset{R^5}{|}} \quad (VI)$$

in which
R⁴ and R⁵ have the abovementioned meaning.

The process according to the present invention for the production of a compound of formula (IV) can be carried out with good yields.

The 5-acyloxy-4(5H)-oxazolonium salts of formula (I) according to the invention are accordingly a novel, valuable class of intermediates, for example for the synthesis of α-ketocarboxylic acid N-acylamides (and—by further hydrolysis—of the corresponding α-ketocarboxylic acids of the formula R¹—CO—COOH, which have diverse uses) and of herbicidally active 1,2,4-triazin-5-one derivatives.

The α-ketocarboxylic acid N-acylamides of formula (V) as such are the subject of U.S. application Ser. No. 235,497, filed Feb. 19, 1981, now pending.

The reaction of these α-ketocarboxylic acid N-acylamides of formula (V) with thiocarbohydrazide (a compound of formula (VI) with R⁴=NH₂ and R⁵=SH) to give triazinones (compounds of formula (IV) with R⁵=SH) is also a subject of an earlier patent application, Ser. No. 235,495, filed Feb. 19, 1981, now pending.

Within the framework of the present invention, the direct reaction of the novel 5-acyloxy-4(5H)-oxazolonium salts of formula (I) with the hydrazine derivatives of formula (VI) to give the desired 1,2,4-triazin-5(4H)-one derivatives of formula (IV) is preferred over the process variant which involves the prior hydrolysis of the salts of formula (I) and intermediate isolation of the α-ketocarboxylic acid N-acylamides of formula (V).

The process described here, proceeding via the novel 5-acyloxy-4(5H)-oxazolonium salts according to the invention, for the preparation of herbicidally active asymmetrical triazinones of formula (IV) is technically superior to the comparable previously known process proceeding via α-ketocarboxylic acid N-tert.-butylamides (see U.S. Pat. Nos. 4,175,188 and 4,224,226).

In particular, the 5-acyloxy-4(5H)-oxazolonium salts of formula (I) according to the invention can be cyclised almost quantitatively, under very mild conditions, with hydrazine derivatives of formula (VI), for example thiocarbohydrazide or S-methyl-thiocarbohydrazide, to give asymmetrical triazinones, which are obtained directly in high purity, whereas the previously known α-ketocarboxylic acid N-tert.-butylamides must, for this purpose, be heated with thiocarbohydrazide for several hours at 100° C., and give yields of only about 70%.

In carrying out the process for the preparation of triazinones from the salts of formula (I) according to the invention, 1 to 1.5 mol of a hydrazine derivative of the formula (VI) are in general employed per mol of a salt of the formula (I). The reaction temperatures are in general between 0° and 100° C., preferably between 15° and 60° C.

For example, the 5-acetoxy-5-tert.-butyl-2-methyl-oxazolonium salt of formula (Ia) gives the herbicidally particularly active compound 4-amino-6-tert.-butyl-3-methylthio-1,2,4-triazin-5(4H)-one of formula (IVb) (compare German Patent Specification No. 1,795,784) in accordance with the following equations:

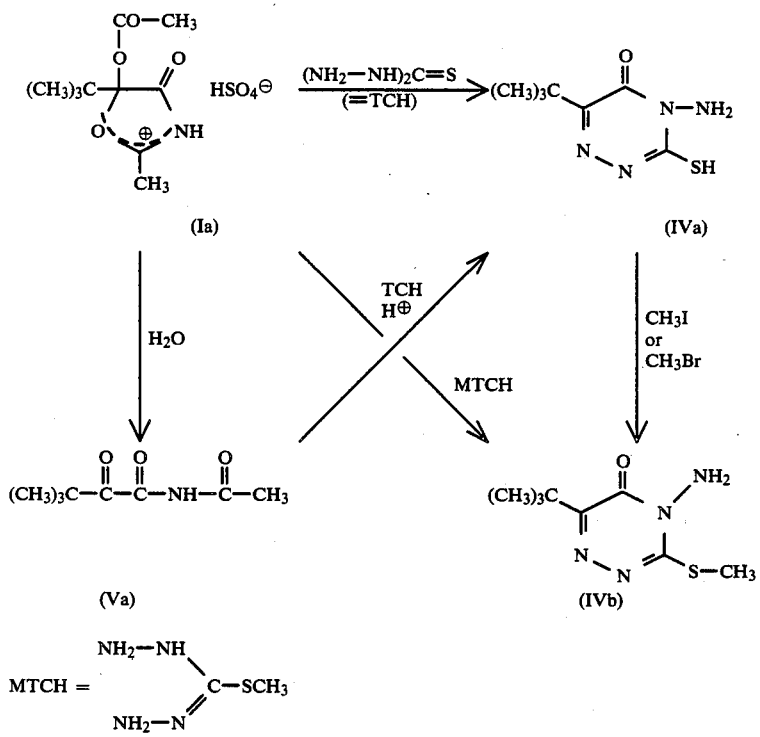

The methylation (IVa)→(IVb) is already known (compare, for example, Chem. Ber. 97, pages 2173-8 (1964); (see U.S. Pat. No. 4,175,188).

The preparative examples which follow illustrate the invention further.

PREPARATIVE EXAMPLES

Example 1

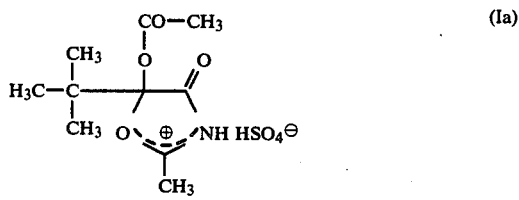

25.6 g of (0.25 mol) of acetic anhydride followed by 27.8 g (0.25 mol) of pivaloyl cyanide were introduced, in each case at room temperature, into 49.0 g (0.5 mol) of concentrated sulphuric acid. After a further 4 hours' stirring, spectroscopic measurements were carried out on the reaction mixture. The characteristic bands of the IR spectrum are shown in Table 1, the signals of the $^1$H-NMR spectrum in Table 2 and the signals of the $^{13}$C-NMR spectrum in Table 3.

Example 2

$$(CH_3)_3C-CO-CO-NH-CO-CH_3 \qquad (Va)$$

25.6 g (0.25 mol) of acetic anhydride, followed by 27.8 g (0.25 mol) of pivaloyl cyanide, were introduced, in each case at room temperature, into 49.0 g (0.5 mol) of concentrated sulphuric acid. After a further 4 hours' stirring, 150 g of ice water were added to the reaction mixture and the batch was stirred thoroughly. The reaction product which precipitated was filtered off, washed with 100 ml of water and dried. 37.0 g (86% of theory) of trimethylpyruvic acid N-acetylamide were obtained as colorless glistening flakes of melting point 82° to 84° C.; purity, according to gas-chromatographic determination, >98%.

Example 3

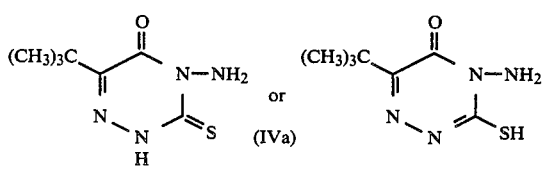

A solution of 5-t-butyl-5-acetoxy-2-methyl-4(5H)-oxazolonium hydrogen sulphate was prepared analogously to Example 1. This solution was then added dropwise to a suspension of 29.3 g (0.275 mol) of thiocarbohydrazide in 300 ml of water, and thereafter the mixture was stirred for one hour at 50° C. It was cooled and the precipitate which had separated out was filtered off and washed until neutral. After drying, 48.0 g (95.9% of theory) of 4-amino-6-t-butyl-3-mercapto-1,2,4-triazin-5(4H)-one were obtained, melting point 212° to 215° C.

Example 4

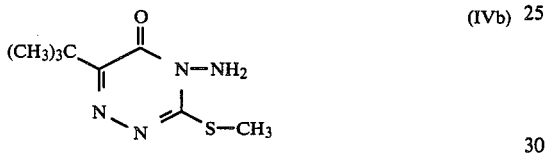

A solution of the oxazolonium hydrogen sulphate of formula (Ia) was prepared analogously to Example 1. This solution was added dropwise to a suspension of 74.4 g (0.3 mol) of S-methylthiocarbohydrazide hydriodide in 300 ml of water and the mixture was then stirred for 0.5 hour at 50° C. An oil separated out, and this was separated off and stirred twice with 100 ml of water. 39.9 g (74.6% of theory) of crude 4-amino-6-t-butyl-3-methylmercapto-1,2,4-triazin-5(4H)-one were obtained. A recrystallized sample melted at 121° to 123° C.

It will be appreciated that the instant specification and examples are set forth by way of illustration and not limitation, and that various modifications and changes may be made without departing from the spirit and scope of the present invention.

We claim:

1. An acidic solution of a 5-acyloxy-4(5H)-oxazolonium salt of the formula

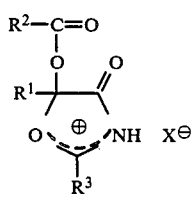

in which $R^1$ represents a straight-chain or branched alkyl group with 1 to 4 carbon atoms optionally substituted by alkoxy with 1 to 4 carbon atoms, carbalkoxy with 1 to 4 carbon atoms in the alkoxy part, nitro, nitrile and/or halogen; represents a cycloalkyl group with 3 to 6 carbon atoms in the ring system which is optionally substituted by alkyl, alkoxy or carbalkoxy, each with up to 4 carbon atoms, nitro, nitrile and/or halogen; represents a phenyl or naphthyl group which is optionally substituted by alkyl, alkoxy or carbalkoxy, each with up to 4 carbon atoms, nitro and/or halogen; or represents a morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl, or furanyl ring which is optionally substituted by alkyl, alkoxy or carbalkoxy, each with up to 4 carbon atoms, nitro, nitrile and/or halogen;

$R^2$ and $R^3$ represent an optionally chlorine-substituted alkyl group with 1 to 4 carbon atoms or a phenyl group, and $X^-$ represents the anion of an inorganic or organic acid having a $pK_a$ value of less than about 2.

2. A solution according to claim 1, wherein such compound is 5-tertiary-butyl-5-acetoxy-2-methyl-4(5H)-oxazolonium hydrogen sulphate.

3. A solution according to claim 1, wherein such compound is 5-phenyl-5-acetoxy-2-methyl-4(5H)-oxazolonium hydrogen sulphate.

4. A solution according to claim 1, wherein such compound is 5-(2-chloro-1,1-dimethyl-ethyl)-5-acetoxy-2-methyl-4(5H)-oxazolonium hydrogen sulphate.

* * * * *